United States Patent
Song et al.

(10) Patent No.: US 6,268,454 B1
(45) Date of Patent: Jul. 31, 2001

(54) AMINO ACID SILICON POLYMER, METHOD FOR PREPARING THE SAME, COSMETIC PARTICLES SURFACE-TREATED WITH THE SAME, AND COSMETIC COMPOSITION CONTAINING THE PARTICLES

(75) Inventors: Dong Hyuk Song; Yeong Jin Choi, both of Kyungki-do; Kil Joong Kim, Seoul; Young Chul Lee, Chungchongbuk-do, all of (KR)

(73) Assignee: Pacific Corporation (KR)

( * ) Notice: Subject to any disclaimer, the term of this patent is extended or adjusted under 35 U.S.C. 154(b) by 0 days.

(21) Appl. No.: 09/506,310

(22) Filed: Feb. 17, 2000

(30) Foreign Application Priority Data

Oct. 6, 1999 (KR) ................................................ 1999-43103

(51) Int. Cl.[7] .............................. C08G 77/06; C08G 77/26
(52) U.S. Cl. ................................ 528/12; 528/14; 528/18; 528/19; 528/26; 528/28; 528/33; 528/36; 528/41; 528/42; 556/413; 556/418; 556/419; 556/420; 556/425
(58) Field of Search ................................ 528/12, 14, 18, 528/19, 26, 28, 33, 36, 41, 42; 556/413, 418, 419, 420, 425

(56) References Cited

U.S. PATENT DOCUMENTS 2,774,778 * 12/1956 Sommer .
5,272,241 * 12/1993 Lucarelli et al. ........................ 528/15
5,399,653 * 3/1995 Lucarelli et al. ........................ 528/28
5,516,869 * 5/1996 Lucarelli et al. ........................ 528/15
5,733,538 * 3/1998 Riffle .................................. 424/78.08

FOREIGN PATENT DOCUMENTS 50-035119 * 4/1975 (JP) .
61-129187 * 6/1986 (JP) .

OTHER PUBLICATIONS

English Abstract of JP–50035119A.*
English Abstract of JP–61129187–A.*

* cited by examiner

Primary Examiner—Robert Dawson
Assistant Examiner—Jeffrey B. Robertson

(57) ABSTRACT

The invention relates to a novel amino acid silicon polymer with good adhesion to the keratin layer of the skin, a method of preparing the amino acid silicon polymer, a cosmetic particles surface-treated with the amino acid silicon polymer, and a color cosmetic composition including the cosmetic particles. According to the present invention, the particles surface-treated up to 3% to the maximum with the amino acid silicon polymer prepared by reacting an amino acid and a functional silicon polymer in the manner of organic synthesis have water resistance and usability peculiar to silicon-treated pigments and take positive surface charges, thereby offering good adhesion to the skin and durability. Due to these characteristics, the cosmetic containing the surface-treated particles of the present invention is superior in the cosmetic effect to that containing the conventional surface-treated particles.

8 Claims, No Drawings

AMINO ACID SILICON POLYMER, METHOD FOR PREPARING THE SAME, COSMETIC PARTICLES SURFACE-TREATED WITH THE SAME, AND COSMETIC COMPOSITION CONTAINING THE PARTICLES

BACKGROUND OF THE INVENTION

1. Field of the Invention

This invention relates to a novel amino acid silicon polymer with good adhesion to the keratin layer of the skin, a method for preparing the amino acid silicon polymer, cosmetic particles surface-treated with the amino acid silicon polymer, and color cosmetic composition containing the cosmetic particles.

2. Background of the Related Art

Color cosmetics are generally used to hide defects of the skin such as freckles and have a fresh and fair complexion. There is a tendency to take the thick cosmetics on the face in order to hide the defects and have a desired complexion. In such a case, a thick make-up layer closes up the skin pores and thereby causes troubles to the skin. It is thus considered that a desirable color cosmetic can be applied to the face very thin and offer an excellent cosmetic effect without troubling the skin. That is, such a good color cosmetic can hide defects of the skin and provide a fair complexion.

Conventionally, examples of cosmetic particles used in color cosmetics include extender pigments such as talc, sericite, mica and kaoline, inorganic coloring pigments such as titanium dioxide, zinc oxide, Prussian blue, deep blue and ferric oxide, and nylon, polyethylene, cellulose or organic tar-based pigments. However, these cosmetic particles come undone off the skin because of weak adhesion to the skin and are easily removed with sweat or water due to low water resistance. The cosmetic particles also have low oil resistance and tend to aggregate with sweat to form a thick cosmetic layer, thereby closing up the skin pores and impairing skin suffocation.

In order to improve such disadvantages of the conventional cosmetic particles, i.e., inferior skin adherence, durability, water resistance and oil resistance, there are generally added a moisturizing agent such as glycerin, sorbitol, propylene glycol and 1,3-butylene glycol, and an oil component such as liquid paraffin, camellia oil, olive oil, evening primrose oil, castor oil, octyl dodecanol and octyl palmitate. However, an excess of the moisturizing agent and the oil component makes the color cosmetics oily and greasy and a lack of them causes the cosmetic particles to come undone off the skin and incurs the dust raising effect.

Accordingly, to overcome the above problems, the articles are surface-treated in an appropriate method. That is, the particles are coated with a moisturizing agent or an oil component or treated with fatty acids, metallic soap of fatty acids, fluorides, silicon, amino acids, or the like. These methods for surface-treating the particles are, however, disadvantageous as follows:

(1) In a method of coating particles with a moisturizing agent, the cosmetic particles thus prepared can be enhanced in the moisture content but easily removed with sweat or water due to low water resistance. Therefore, this method is inapplicable to cosmetics for the summer.

(2) In a method of coating particles with an oil component or a fatty acid, the cosmetic particles thus prepared can be enhanced in water resistance, thereby generating intense repulsion to water, but easily thickened due to such a low oil resistance as to aggregate the particles with the oil component of the sweat. Such particles applied to the skin form a thick make-up layer, thus closing up the skin pores and impairing skin suffocation, and deteriorate durability of the cosmetic as to cause the cosmetic powder to come undone off the skin and aggregate after an elapse of long time.

(3) In a method of treating particles with fluorides, the cosmetic particles thus prepared can have good water resistance and oil resistance. Yet, such cosmetic particles are inferior in particle-skin adhesion as well as particle-particle adhesion. Hence, the cosmetic particles applied to the face tend to come undone off the skin and cause the dust raising effect.

(4) In a method of surface-treating particles with silicon, the cosmetic particles thus prepared are excellent in water resistance, dispersion and usability but inferior in the affinity to bio-components constituting the skin, thereby causing extraneousness. Further, the cosmetic layer is easy to become undone off the skin and the pigment particles easily aggregate.

(5) In a method of surface-treating particles with a derivative of amino aced such as lysine or glutamic acid in an aqueous dispersion solution, as disclosed in EU Patent No. 139481, the cosmetic particles thus prepared have good affinity to the skin, hence good adhesion but are easily removed with water due to low water resistance.

As described above, amino acids and their derivatives have been conventionally used to provide affinity to the skin for the pigment of color cosmetics. Examples of the amino acid include N-acylated derivatives of L-lysine (i.e., basic amino acids) and of glutamic acid (i.e., acidic amino acids). Such an amino acid treated pigment is superior in adherence to the skin to other pigments but easily removed with water. Thus, the amino acid treated pigment is hard to mix in a large amount with color cosmetics that require good durability.

On the other hand, there is a case where an inorganic pigment is treated with a mixture of perfluoroalkyl phosphate as a fluoride component and lauroyl lysine as an amino acid component. Such a composite pigment improves deterioration of adhesion to the skin but requires a large amount of coating that increases entirely the content of the two processing agents in excess of 5% of the pigment. Coating with an excess of such processing agents makes the coating inhomogeneous to entirely impair the cosmetic effect and results in a compression-molded formulation excessively hard. Thus, it becomes difficult to control the pay-off amount of the cosmetic particles by means of a cosmetic tool such as powder puff or tip.

Alternatively, EU Patent No. 725056 discloses a method for preparing fluoroalkyloxycarbonyl lysine chemically synthesized from a fluoride group as a fluoride component and an amino acid, and a method for surface-treating an inorganic pigment.

A composite surface treatment method using fluorides and an inorganic pigment surface treatment method using a novel surface treatment agent effectively improve the disadvantage of the surface treatment method using fluorides, i.e., deterioration of affinity to the skin. However, the methods are inapplicable to a cosmetic requiring usability, since the fluoride derivative as a pigment treatment agent is not excellent in the lubricating ability. Furthermore, the cosmetic prepared by the method is a solid containing the treatment agent having a melting point of higher than 200° C. and thereby is inferior in the usability to the liquid-state cosmetic surface-treated with silicon that has a good lubricating ability at a room temperature.

The keratin layer constituting the outermost layer of the skin is a layer in direct contact with the color cosmetic particles. It is known that the keratin layer is a slightly acidic and negatively charged. However, an inorganic extender pigments such as talc, mica, sericite and kaoline and a pigment surface-treated with silicon, fluoride and metallic soap, as conventionally applied to the cosmetic particles, are negatively charged or take no surface charges and thus difficult to adhere to the skin in an electrostatic manner. And, the adhesion of these color cosmetics primarily depends on the viscosity and the liquidity of binding oil such as mineral oil, fatty acid ester and dimethyl polysiloxane. The binding oil is absorbed in the skin over time after taking a make-up and has a deterioration of binding performance after an elapse of time, so that the cosmetic particles aggregating and coming undone from the skin are easily removed. Therefore, adhesion of the pigment by the binding oil adversely results in deterioration of the affinity of the cosmetic to the skin due to a lack in electrostatic bonding, thus inefficiently providing an effect of the surface treatment agent.

SUMMARY OF THE INVENTION

Under such circumstances, the inventor has made intensive studies to develop a method for preparing improved color cosmetic particles. Therefore, the invention is directed to provide an amino acid silicon polymer as a novel surface treatment agent that still offers the advantages of silicon such as good usability and water resistance and takes positive charges such that it can adhere to the negatively charged surface of the skin in an electrostatic manner, and to further provide cosmetic particles surface-treated with such an amino acid silicon polymer.

Accordingly, it is an object of the present invention to provide a method for preparing a novel amino acid silicon polymer having both terminals substituted by amino acids by reacting a silicon polymer containing silanol groups at both terminals thereof with an amino acid in an organic synthetic manner.

It is another object of the present invention to provide a method for preparing surface-treated particles having high affinity to the skin by coating a small amount of an amino acid silicon polymer on the surface of dry particles such as extender pigment, white pigment, inorganic coloring pigment and organic lake colorants.

It is further another object of the present invention to provide a color cosmetic composition having high affinity to the skin as well as good water resistance and spreadability by adding cosmetic particles surface-treated with the amino acid silicon polymer.

DETAILED DESCRIPTION OF THE INVENTION

This invention relates to a novel amino acid silicon polymer with good adhesion to the keratin layer of the skin, a method of preparing the amino acid silicon polymer, cosmetic particles surface-treated with the amino acid silicon polymer, and a color cosmetic composition containing the cosmetic particles.

The present invention is directed to provide a novel amino acid polymer as a surface treatment agent for particles, which is prepared by chemically coupling one of naturally existing amino acids or a mixture of them, to both terminals of a reactive silicon polymer or its derivative, thereby having both the physical properties of amino acid and the properties of silicon in a single material.

The novel amino acid silicon polymer can be produced by the two following preparation methods.

The first method to produce the novel amino acid silicon polymer involves a process of heating dimethyl polysiloxanol with a viscosity ranging from 20 cps to 20,000 cps and one of acidic amino acids containing a carboxyl group at the residue thereof or at least two of them in an organic solvent in the presence of a catalyst, thereby inducing esterification between hydroxy groups at both terminals of the dimethyl polysiloxanol and a carboxyl group of the acidic amino acid.

As shown in the formula 1, the dimethyl polysiloxanol is a reactive silicon polymer having both terminals substituted by silanols.

[Formula 1]

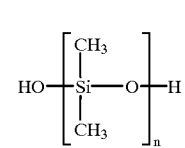

wherein the polymerization degree "n" is an integer from 1 to 1000.

Examples of the amino acid used in the first preparation method include acidic amino acids having carboxyl groups, as expressed by the formula 2, and preferably, glutamic acid and aspartic acid.

[Formula 2]

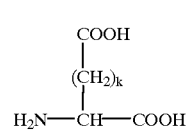

wherein k is 1 or 2.

In the first preparation method, a compound having the formula 3 or 4 can be produced by esterification of one amino acid, that is, glutamic acid (when k=1 in the formula 2) or aspartic acid (when k=2 in the formula 2) with the dimethyl polysiloxanol.

[Formula 3]

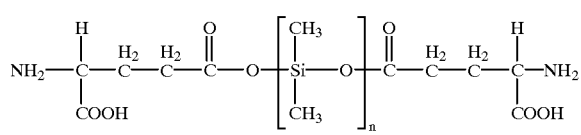

wherein the polymerization degree "n" is an integer from 1 to 1000.

[Formula 4]

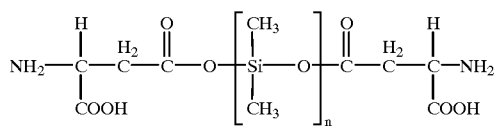

wherein the polymerization degree "n" is an integer from 1 to 1000.

On the other hand, the amino acid silicon polymer generally produced by reacting one of the acidic amino acids having carboxyl groups (—COOH) as shown in the formula 2 or a mixture of them with the dimethyl polysiloxanol can be expressed by the formula 5.

[Formula 5]

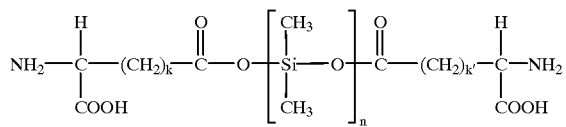

wherein the polymerization degree "n" is an integer from 1 to 1000, and k and k' are independently 1 or 2.

Examples of the organic solvent include benzene, toluene, xylene, 1,4-dioxane, chloroform and 1,2-dichloroethane. These organic solvents have a boiling point of greater than 70° C. and contain no hydroxy group.

Examples of the catalyst include any catalysts that are commonly used in the esterification, such as sulfuric acid, paratoluene sulfonic acid, methane sulfonic acid, tin, zinc, titanium, organic titanium, organic tin, zinc oxide, magnesium oxide and calcium oxide. The concentration of the catalyst is preferably 0.05~0.5%.

The second method to produce the novel amino acid silicon polymer involves processes of: (a) reacting hydroxy groups of dimethyl polysiloxanol having the formula 1 with two equivalents of chloroacetic acid in an organic solvent in the presence of an acidic catalyst to produce dimethyl polysiloxane dichloroacetate expressed by the formula 6; and (b) substituting chlorine atoms of the dimethyl polysiloxane dichloroacetate of the formula 6 by amino groups of a basic amino acid expressed by the formula 7, such as arginine, asparagines or lysine.

[Formula 6]

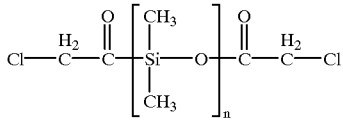

wherein the polymerization degree "n" is an integer from 1 to 1000.

[Formula 7]

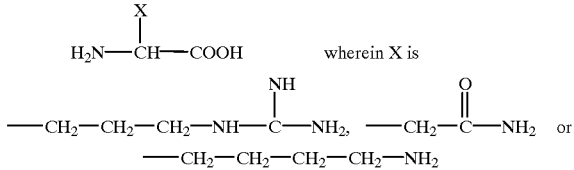

In the second preparation method, a compound of the formula 8, 9 or 10 can be produced when one of the basic amino acids including arginine, asparagine and lysine is reacted with the dimethyl polysiloxane dichloroacetate.

[Formula 8]

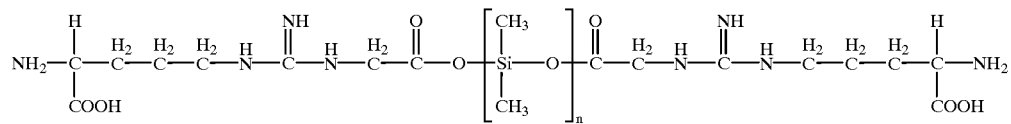

wherein the polymerization degree "n" is an integer from 1 to 1000.

[Formula 9]

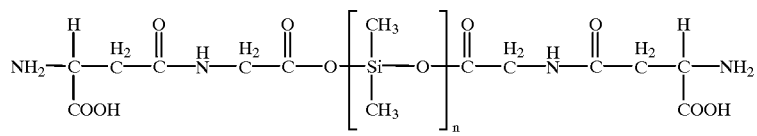

wherein the polymerization degree "n" is an integer from 1 to 1000.

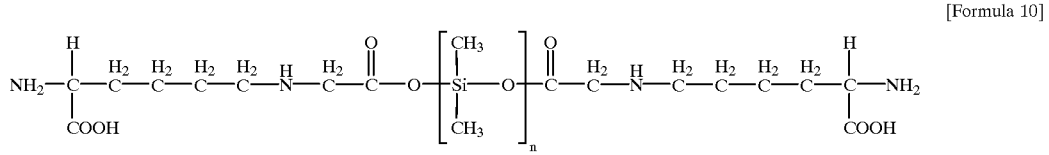

[Formula 10]

wherein the polymerization degree "n" is an integer from 1 to 1000.

On the other hand, the amino acid silicon polymer generally produced by reacting one of the basic amino acids having the formula 7 or a mixture of them with the dimethyl polysiloxane dechloroacetate can be expressed by the formula

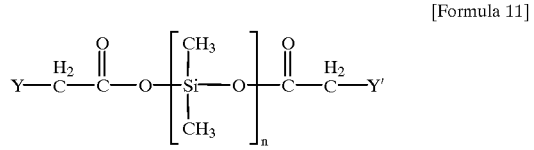

[Formula 11]

wherein the polymerization degree "n" is an integer from 1 to 1000, and Y and Y' are independently

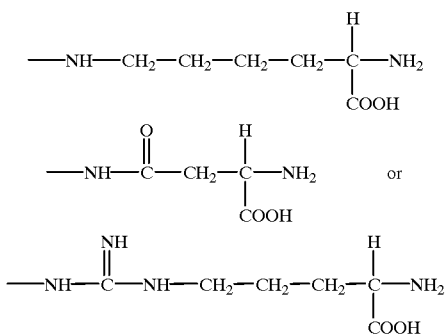

Examples of the acidic catalyst include sulfuric acid, hydrochloric acid, nitric acid, phosphoric acid, paratoluene sulfonic acid, and methane sulfonic acid.

Examples of the organic solvent include polar solvents such as methanol, ethanol, propanol, isopropanol, butanol and acetone.

Examples of the slightly basic catalyst include sodium carbonate, sodium bicarbonate, and potassium carbonate. The added amount of the slightly basic catalyst is 5~100 wt. %.

Examples of the method for surface-treating cosmetic particles using the amino acid silicon polymer prepared in the present invention include a wet method and a dry method depending on desired usability and expediency of the preparation process.

In the wet method, cosmetic particles such as talc, sericite, mica, kaoline, boron nitride, titanium dioxide, and zinc oxide are dispersed in an acidic solution at pH 3.5~5.5. Examples of the acid used herein include hydrochloric acid, sulfuric acid, nitric acid, phosphoric acid, acetic acid, and lactic acid. The acid solution can be controlled to have a desired pH, with a buffer solution of acetic acid or phosphoric acid.

A solution prepared by completely dissolving the amino acid silicon polymer and a surfactant with the HLB value of 8~18 in an organic solvent is added, while vigorously stirring a pigment dispersed solution at greater than 300 rpm. The mixture is then agitated and quenched. When the viscosity of the mixed solution ceases to increase, the dispersed solution is removed of water and the solvent through vacuum filtration and is dried with hot air at 120° C. for 24 hours, thereby producing particles surface-treated with the amino acid silicon polymer.

Examples of the surfactant having the HLB value of 8~18 include PEG-40 stearate, PEG-100 stearate, octyldodeseth-16, PEG-20 hydrogenated castor oil, PEG-60 hydrogenated castor oil, PEG-8 dilaurate, polysorbate 20, polysorbate 60, and polysorbate 80. The surfactant is preferably added in an amount of 0.1~50 wt. % based on 100 wt. % of the amino acid silicon polymer.

In the dry method, while vigorously stirring particles with a high-speed agitator, the amino acid silicon polymer, or a mixed solution of the amino acid silicon polymer and an alcohol-based organic solvent having the boiling point of below 70° C. or volatile silicon is added in the method of spray. The mixture is dried to produce surface-treated particles.

Thus surface-treated particles still have advantages of the related art silicon-treated particles, such as high water resistance, lubricating ability and spreadability and overcome disadvantages of the silicon-treated particles, such as aridity and dusting, thereby providing enhanced adhesion to the skin and formability. This enhancement of adhesion to the skin results from the particle surface treatment using the cationic amino acid silicon polymer.

The color cosmetic composition of the present invention includes particles surface-treated with the amino acid silicon polymer prepared by the above-stated method. The added amount of the above surface-treated particles can be determined appropriately according to the formulation and is preferably 0.05~80 wt. % based on 100 wt. % of the cosmetic composition.

Although there is no particular limitation imposed on the formulation of the color cosmetic composition in the present invention, specific examples include twin cake, cream foundation, make-up base, lips stick, eye shadow, brusher, and compact.

The cosmetic composition of each formulation may further include other components rather than the cosmetic particles surface-treated with the amino acid silicon polymer. These additional components are appropriately selected by those who are skilled in the related art according to the formulation and the purpose of usage.

Hereinafter, a detailed description of the present invention will be made in connection with the following embodiments. The present invention should not be, however, limited thereto.

Embodiment 1: Preparation of Amino Acid Silicon Polymer (1) 800 g of toluene, 100 g of dimethyl polysiloxanol (average molecular weight 1000 g/mol, polymerization degree (n)=13, viscosity=30 cps) and 29.4 g of L-glutamic acid were added in a three neck flask having a Dean Stark Trap, a thermometer and a condensing tube.

(2) 0.5 g of 95% sulfuric acid was added to the resulting material of the above step (1). The mixture was then subjected to a reflux reaction under stirring.

(3) Water was eliminated as much as a theoretical amount of water after an elapse of 5 hours since waterdrops started to form on the Dean Stark Trap at the reaction temperature of 120° C.

(4) The reactant solution was cooled to 30° C. in a water bath. 300 g of sodium carbonate was then added to neutralize the sulfuric acid and the mixture was filtered under vacuum.

(5) The filtrate was concentrated under vacuum and the toluene was removed. As a result, there was obtained a colorless and odorless glutamic acid silicon polymer having a viscosity of 23,000 cps at a room temperature.

Embodiments 2 to 6: Preparation of Amino Acid Silicon Polymer

Amino acid silicon polymers of Embodiments 2 to 6 were prepared in the same manner as Embodiment 1 except for the type and the added amount of amino acid and the polymerization degree "n" of dimethyl polysiloxanol, as listed in Table 1.

TABLE 1

| Embodiments | Dimethyl Polysiloxanol | | Amino Acid | |
|---|---|---|---|---|
| | Polymerization Degree (n) | Added Amount (g) | Type | Added Amount (g) |
| Embodiment 2 | 20 | 100 | L-Glutamic Acid | 18.5 |
| Embodiment 3 | 100 | 100 | L-Glutamic Acid | 3.8 |
| Embodiment 4 | 13 | 100 | L-Asparagine | 26.6 |
| Embodiment 5 | 20 | 100 | L-Asparagine | 17.3 |
| Embodiment 6 | 100 | 100 | L-Asparagine | 3.5 |

The IR spectrums of the glutarmic acid silicon polymers Embodiments 1, 2 and 3 were:

704 (w), 797 (s), 867 (m), 1018 (s), 1090 (s), 1260 (s), 1414 (w), 1445 (w), 2907 (w), 2966 (s) cm$^{-1}$

The IR spectrums of the asparagine acid silicon polymers in Embodiments 4, 5 and 6 were:

694 (w), 792 (s), 870 (m), 1007 (s), 1087 (s), 1189 (s), 1421 (w), 1456 (w), 2911 (w), 2981 (s) cm$^{-1}$

Embodiment 7: Preparation of Amino Acid Silicon Polymer (1) 800 g of toluene, 100 g of dimethyl polysiloxanol (average molecular weight 1000 g/mol, polymerization degree (n)=13, viscosity=30 cps) and 18.9 g of acetic acid were added in a three neck flask having a Dean Stark Trap, a thermometer and a condensing tube.

(2) 0.5 g of 95% sulfuric acid was added to the resulting material of the above step (1). The mixture was then subjected to a reflux reaction under stirring.

(3) Water was eliminated as much as a theoretical amount of water after an elapse of 3 hours since waterdrops started to form on the Dean Stark Trap at the reaction temperature of 120° C.

(4) The reactant solution was cooled to 30° C. in a water bath and 300 g of sodium carbonate was added to neutralize the sulfuric acid. The mixture was then filtered under vacuum.

(5) The filtrate was concentrated under vacuum and the toluene was removed. As a result, there was obtained liquid dimethyl polysiloxane dichloroacetate having a peculiar odor and a viscosity of 18 cps at a room temperature.

(6) 100 g of the dimethyl polysiloxane dichloroacetate, 25.2 g of L-lysine, 200 g of potassium carbonate and 500 g of ethanol were added in a two neck flask connected to a thermometer and a condensing tube.

(7) The extent of reaction was determined through quantitative analysis of chlorine ions while stirring the mixture at the room temperature.

(8) After an elapse of 6 hours, the ethanol was vaporized under vacuum and 200 g of water and 200 g of ethyl acetate were added so as to separate the mixture into an aqueous layer and an organic layer.

(9) The organic layer was collected and vaporized under vacuum to yield a colorless and odorless lysine silicon polymer having a viscosity of 18,000 cps at the room temperature.

Embodiments 8 to 15: Preparation of Amino Acid Silicon Polymer

Amino acid silicon polymers of Embodiments 8 to 15 were prepared in the same manner as Embodiment 7 except for the type and the added amount of amino acid, the amount of chloroacetic acid, and the polymerization degree "n" of dimethyl polysiloxanol, as listed in Table 2.

TABLE 2

| Embodiments | Dimethyl Polysiloxanol | | Choloracetic Acid Added Amount (g) | Amino Acid | |
|---|---|---|---|---|---|
| | Polymerization Degree (n) | Added Amount (g) | | Type | Added Amount (g) |
| Embodiment 8 | 20 | 100 | 12.3 | L-Lysine | 16.4 |
| Embodiment 9 | 100 | 100 | 2.5 | L-Lysine | 3.3 |
| Embodiment 10 | 13 | 100 | 18.9 | L-Arginine | 30.2 |
| Embodiment 11 | 20 | 100 | 12.3 | L-Arginine | 19.7 |
| Embodiment 12 | 100 | 100 | 2.5 | L-Arginine | 3.9 |
| Embodiment 13 | 13 | 100 | 18.9 | L-Asparagine | 27.7 |
| Embodiment 14 | 20 | 100 | 12.3 | L-Asparagine | 18 |
| Embodiment 15 | 100 | 100 | 2.5 | L-Asparagine | 3.6 |

The IR spectrums of the lysine silicon polymers in Embodiments 7, 8 and 9 were:

703 (s), 799 (s), 865 (w), 1021 (s), 1263 (s), 1413 (w), 2906 (w), 2965 (s) cm$^{-1}$

The IR spectrums of the arginine silicon polymers in Embodiments 10, 11 and 12 were:

701 (s), 791 (s), 865 (w), 1027 (s), 1269 (s), 1407 (w), 2884 (w), 2948 (s) cm$^{-1}$

The IR spectrums of the asparagine silicon polymers in Embodiments 13, 14 and 15 were:

699 (s), 789 (s), 871 (w), 1017 (s), 1259 (s), 1411 (s), 1524 (w), 2901 (w), 2971 (s) cm$^{-1}$

Embodiment 16: Method of Surface-Treating Particles with Amino Acid Silicon Polymer (1) 50 g of 3% hydrochloric acid solution was added to 400 g of purified water. 100 g of talc was further added as particles. The mixture was then agitated while maintaining its temperature at 65° C.

(2) 2.5 g of the glutamic acid silicon polymer prepared in Embodiment 1 and 0.5 g of PEG-40 stearate were added to 15 g of isopropyl alcohol. The mixture was heated at 60° C. to dissolve the glutamic acid silicon polymer and the PEG-40 stearate in the isopropyl alcohol, thereby producing a surface treatment agent.

(3) The surface treatment agent prepared in the step (2) was gradually added to the aqueous particles obtained in the step (1). The mixture was agitated for 1 hour and quenched to a temperature of below 30° C. at a cooling rate of greater than 1° C./min.

(4) The resulting material of the step (3) was stationed for more than 12 hours, filtered and was dried with hot air at 100~120° C. for 6 hours. As a result, there was obtained particles surface-treated with the glutamic acid silicon polymer.

Embodiment 17: Surface-Treatment Particles with Amino Acid Silicon Polymer

Particles surface-treated with lysine silicon polymer were prepared in the same manner as Embodiment 16 except for using the lysine silicon polymer of Embodiment 7 and 0.1 g of PEG-20 hydrogenated castor oil instead of the glutamic acid silicon polymer and 0.5 g of the PEG-40 stearate in the step (2).

Embodiment 18: Surface Treatment of Particles with Amino Acid Silicon Polymer (1) 100 g of mica was added as particles in a high-speed mixer.

(2) 3 g of the glutamic acid silicon polymer prepared in Embodiment 1 was mixed with 3 g of volatile silicon. The mixture was heated at 70° C. and completely dissolved, thereby producing a surface treatment agent.

(3) While the resulting material of the step (1) was agitated at a high speed of 5000 rpm, the surface treatment agent of the step (2) was added to the resulting material through dry fog injection and mixed for 5 minutes.

(4) The volatile silicon was removed from the resulting material of the above step (3) through the hot air drying for more than 6 hours. As a result, there were obtained particles surface-treated with the glutamic acid silicon polymer.

Embodiment 19: Surface Treatment of Particles with Amino Acid Silicon Polymer

The particles surface-treated with the lysine silicon polymer were prepared in the same manner as Embodiment 18 except for using the lysine silicon polymer prepared in Embodiment 7 instead of the glutamic acid silicon polymer in the step (2) of Embodiment 18.

Comparative Example 1

This example used raw talc that has not undergone a surface treatment.

Comparative Example 2

(1) 100 g of talc was added as particles to 400 g of purified water. The mixture was then agitated while maintaining its temperature at 65° C.

(2) 3 g of dimethicone was added to 15 g of isopropylalcohol. The mixture was heated at 60° C. to dissolve the dimethicone in the isopropylalcohol, thereby preparing a surface treatment agent.

(3) The surface treatment agent of the above step (2) was gradually added to the aqueous particles of the above step (1). The mixture was agitated for 1 hour and then quenched to below 30° C. at a cooling rate of greater than 1° C./min.

(4) The resulting material of the above step (3) was stationed for more than 12 hours, was filtered and was dried with hot air at 100~120° C. for more than 6 hours. As a result, particles surface-treated with the dimethicone were obtained.

Comparative Example 3

(1) 100 g of talc was added as particles to 400 g of purified water. The mixture was then agitated while maintaining its temperature at 40° C.

(2) 3 g of N-lauroyl L-lysine was added to 20 g of 5% NaOH aqueous solution. The mixture was heated at 60° C. to dissolve the N-lauroyl L-lysine in the NaOH aqueous solution, thereby preparing a surface treatment agent.

(3) The surface treatment agent of the above step (2) was gradually added to the aqueous particles of the above step (1). 20 g of 10% HCl solution was further added to the mixture.

(4) The mixture was agitated for 1 hour and then quenched to below 30° C. at a cooling rate of greater than 1° C./min.

(5) The resulting material of the above step (3) was stationed for more than 12 hours, was filtered and was dried with hot air at 100~120° C. for more than 6 hours. As a result, particles surface-treated with the amino acid derivative, L-lauroyl L-lysine were obtained.

Comparative Example 4

Particles surface-treated with an amino acid derivative, cocoyl glutamate were prepared in the same manner as Comparative Example 3, except for using cocoyl glutamate instead of the N-lauroyl L-lysine in step (1) of Comparative Example 3.

Experimental Example 1

Measurement of Zeta Potential

Zeta potentials of the respective products of Embodiments 16 and 17 and Comparative Examples 1 to 4 were measured with an ELS-8000 (Photal) zeta potentiometer under the neutrality condition and the weak acid condition of pH=5.5 similar to the skin condition, so as to analyze the products in regard to their electrostatic affinity to the skin. The results are shown in Table 3.

TABLE 3

| Samples | Zeta Potential (mV) | |
|---|---|---|
| | pH = 7 | pH = 5.5 |
| Embodiment 16 | +15.36 | +32.24 |
| Embodiment 17 | +12.76 | +27.92 |
| Comparative Example 1 | −24.70 | −2.44 |
| Comparative Example 2 | −7.11 | +11.23 |
| Comparative Example 3 | +26.80 | +41.27 |
| Comparative Example 4 | +22.71 | +38.91 |

As understood from the zeta potentials of the pigment surface as shown in Table 3, the surface charges of all samples excepting those of Comparative Example 1 (i.e., non-surface-treated particles) were positive at the pH of the skin.

The samples of Comparative Example 1 (i.e. non-surface-treated particles) and Comparative Example 2 (i.e., silicon-treated particles) had negative surface charges. From this, it can be expected that the products of Comparative Examples 1 and 2 have their affinity to the skin deteriorated. The particles surface-treated with amino acids as prepared in Comparative Examples 3 and 4 had positive surface charges. Likewise, the particles of Embodiments 16 and 17 had positive surface charges. These results totally conformed the objects of the present invention.

Experimental Example 2

Test for Adhesion to Keratin

Adhesions to the outermost layer of the skin, keratin layer were measured with a Seishin MT-1000 instrument for measuring physicochemical properties of particles, for the respective samples of Embodiments 16 and 17 and Comparative Examples 1 to 4 and for the samples prepared by mixing the above samples with keratin particles at the ratio of 1:1. The measurement was performed in such a manner that the sample powder of a predetermined volume was dropped several times by a predetermined force and the decreased volume of the sample powder was measured. The measured values were used to calculate an adhesion coefficient 1/b according to the Kitakawa equation [$N/C=(1/ab)+(1/a)N$, where N is the number of tapping time; C is a ratio of volume reduction; "a" is a coefficient representing most-densely-filled specific volume].

Here, the adhesion coefficient of the sample alone represents particle-particle adhesion and the adhesion coefficient of the sample-keratin mixture represents particle-skin adhesion.

The results are listed in Table 4.

TABLE 4

| Samples | Particle-Particle Adhesion Coefficient (1/b) | Sample-Keratin Adhesion Coefficient (1/b) | Particle-Skin Adhesion Coefficient (1/b) |
| --- | --- | --- | --- |
| Embodiment 16 | 42.6 | Embodiment 16 + Keratin | 67.5 |
| Embodiment 17 | 36.7 | Embodiment 17 + Keratin | 48.1 |
| Comparative Example 1 | 31.5 | Comparative Example 1 + Keratin | 29.6 |
| Comparative Example 2 | 25.9 | Comparative Example 2 + Keratin | 32.1 |
| Comparative Example 3 | 38.6 | Comparative Example 3 + Keratin | 54.6 |
| Comparative Example 4 | 43.2 | Comparative Example 4 + Keratin | 47.9 |

As understood from the adhesion coefficients as shown in Table 4, the samples of Embodiments 16 and 17 were much more excellent in both particle-particle adhesion and particle-skin adhesion than those of Comparative Examples 1 and 2, and similar or superior to those of Comparative Examples 3 and 4. This demonstrates that the embodiments of the present invention provide excellent adhesion to the real skin as intended by the inventor.

Experimental Example 3

Test for Water Resistance

Procedures for measuring water resistance of the samples of Embodiments 16 and 17 and Comparative Examples 1 to 4 were performed as follows.

100 g of an aqueous solution of acetone was added to a 100 ml beaker. The composition of the acetone was adjusted in terms of weight %. A sample to be measured was dropped in a small amount to form a thin particle layer on the surface of the solution, and pulses were applied with a Seishin IH-2000 horizontal pulse oscillator. Here, while varying the amount of the acetone by 1 g, the weight ratio of the acetone was measured when the sample is dropped into the solution, during oscillation of 1 minute. When the particles start to disperse, the surface tension of the aqueous solution of acetone can be considered as the critical surface tension of the particles. Thus, the weight ratio of the acetone can be expressed in terms of the water resistance of the sample, This test was repeatedly carried out five times for every sample. Ignoring the highest and lowest values, the measured values obtained from three times of the test were averaged. The results are listed in Table 5.

TABLE 5

| Samples | Weight Ratio of Acetone (Water Resistance) |
| --- | --- |
| Embodiment 16 | 43% |
| Embodiment 17 | 38% |
| Comparative Example 1 | 17% |
| Comparative Example 2 | 45% |
| Comparative Example 3 | 26% |
| Comparative Example 4 | 20% |

As shown in Table 5, the talc particles surface-treated with the amino acid silicon polymer according to the present invention (Embodiments 16 and 17) were not significantly different in water resistance from the talc particles surface-treated with the dimethicone (Comparative Example 2), and remarkably superior in water resistance to the non-surface-treated talc particles (Comparative Example 1) and the pigment particles surface-treated with amino acids (Comparative Examples 3 and 4).

Preparation Examples 1 and 2, and Comparative Preparation Examples 1 to 4

Preparation of Powder Foundation

Particles of Embodiments 16 and 17 and Comparative Examples 1 to 4 were processed into formulations of powder foundation according to the preparation formulas as shown in Table 6.

TABLE 6

| Components | A1 | A2 | B1 | B2 | B3 | B4 |
| --- | --- | --- | --- | --- | --- | --- |
| 1. Embodiment 16 | ~100 | — | — | — | — | — |
| 2. Embodiment 17 | — | ~100 | — | — | — | — |
| 3. Comparative Example 1 | — | — | ~100 | — | — | — |

TABLE 6-continued

| Components | A1 | A2 | B1 | B2 | B3 | B4 |
|---|---|---|---|---|---|---|
| 4. Comparative Example 2 | — | — | — | ~100 | — | — |
| 5. Comparative Example 3 | — | — | — | — | ~100 | — |
| 6. Comparative Example 4 | — | — | — | — | — | ~100 |
| 7. Nylon | 5.0 | 5.0 | 5.0 | 5.0 | 5.0 | 5.0 |
| 8. Starch | 3.0 | 3.0 | 3.0 | 3.0 | 3.0 | 3.0 |
| 9. Titanium Dioxide | 3.0 | 3.0 | 3.0 | 3.0 | 3.0 | 3.0 |
| 10. Ferric Oxide Pigment | 3.0 | 3.0 | 3.0 | 3.0 | 3.0 | 3.0 |
| 11. Mica | 25.0 | 25.0 | 25.0 | 25.0 | 25.0 | 25.0 |
| 12. Squalene | 0.5 | 0.5 | 0.5 | 0.5 | 0.5 | 0.5 |
| 13. Dimethicone | 0.8 | 0.8 | 0.8 | 0.8 | 0.8 | 0.8 |
| 14. Preservative | 0.1 | 0.1 | 0.1 | 0.1 | 0.1 | 0.1 |
| 15. Aromatics | Microdose | Microdose | Microdose | Microdose | Microdose | Microdose |

Note)
A1: Preparation Example 1
A2: Preparation Example 2
B1: Comparative Preparation Example 1
B2: Comparative Preparation Example 2
B3: Comparative Preparation Example 3
B4: Comparative Preparation Example 4

(1) Components 1 to 11 were powdered once with a hammer-type powdering machine.

(2) The resulting material of the above step (1) was vigorously mixed for 5 minutes in a high-speed mixer.

(3) Components 12 to 15 were mixed with the resulting material of the step (2) and heated.

(4) The resulting material of the step (3) was vigorously mixed for 5 minutes in the high-speed mixer.

(5) The resulting material of the step (4) was powdered twice with the hammer-type powdering machine.

Experimental Example 4

Sensory Test for Usability

For the powder foundations prepared in Preparation Examples 1 and 2 and Comparative Preparation Examples 1 to 4, adherence, water resistance, durability and use feeling were measured. In the measurement method, a panel of 50 experts in their early twenties to middle forties used the powder foundations for one month and appraised the adherence, water resistance, durability and use feeling of the powder foundations on five levels. The results are averaged and listed in Table 7.

TABLE 7

| | A1 | A2 | B1 | B2 | B3 | B4 |
|---|---|---|---|---|---|---|
| Adherence | 4.8 | 4.7 | 4.0 | 3.6 | 4.5 | 4.8 |
| Water Resistance | 4.5 | 4.6 | 3.4 | 4.7 | 3.9 | 3.6 |
| Durability | 5.0 | 4.9 | 3.8 | 4.3 | 4.0 | 3.8 |
| Use Feeling | 4.8 | 4.7 | 4.4 | 4.6 | 4.1 | 3.9 |

TABLE 7-continued

| | A1 | A2 | B1 | B2 | B3 | B4 |
|---|---|---|---|---|---|---|
| Appraisal Criterion | | | 1 2 3 4 5 | | | |
| | | Worst | | | Best | |

Note)
A1: Preparation Example 1
A2: Preparation Example 2
B1: Comparative Preparation Example 1
B2: Comparative Preparation Example 2
B3: Comparative Preparation Example 3
B4: Comparative Preparation Example 4

As shown in Table 7, the powder foundations of Preparation Examples 1 and 2 prepared using the particles of Embodiments 16 and 17 were appraised excellent evenly in every test items, entirely improving cosmetic effects, compared to those of Comparative Preparation Example 1 (i.e., using the non-treated particles), Comparative Preparation Example 2 (i.e., using the particles surface-treated with dimethicone) and Comparative Preparation Examples 3 and 4 (i.e., using the particles surface-treated with amino acids).

Preparation Examples 3 and 4

Preparation of Eye Shadow

Pigments of Embodiments 16 and 17 were processed into formulations of eye shadow according to the preparation formulas as shown in Table 8.

TABLE 8

| Components | Preparation Example 3 | Preparation Example 4 |
|---|---|---|
| 1. Embodiment 16 | ~100 | — |
| 2. Embodiment 17 | — | ~100 |
| 3. Sericite | 10.0 | 10.0 |
| 4. Mica | 15.0 | 15.0 |
| 5. Titanium Mica | 15.0 | 15.0 |
| 6. Ferric Oxide Pigment | 30.0 | 30.0 |
| 7. Cetiol-A | 1.3 | 1.3 |
| 8. Cosmol-222 | 1.0 | 1.0 |
| 9. Preservative | 0.1 | 0.1 |
| 10. Aromatics | Microdose | Microdose |

(1) Components 1 to 6 were powdered once with a hammer-type powdering machine.

(2) The resulting material of the above step (1) was vigorously mixed for 5 minutes in a high-speed mixer.

(3) Components 7 to 10 were mixed with the resulting material of the step (2) and heated.

(4) The resulting material of the step (3) was vigorously mixed for 5 minutes in the high-speed mixer.

(5) The resulting material of the step (4) was powdered twice with the hammer-type powdering machine.

(6) 2 g of the resulting material of the step (5) was added in a 3.4 cm-diameter and 0.7 cm-deep container, was compressed under a pressure of 20 kg/cm$^2$, and was molded.

Preparation Examples 5 and 6

Preparation of Face Powder

Pigments of Embodiments 16 and 17 were processed into formulations of face powder according to the preparation formulas as shown in Table 9.

TABLE 9

| Components | Preparation Example 5 | Preparation Example 6 |
|---|---|---|
| 1. Embodiment 16 | ~100 | — |
| 2. Embodiment 17 | — | ~100 |
| 3. Sericite | 17.0 | 17.0 |
| 4. Starch | 15.0 | 15.0 |
| 5. Silica | 11.0 | 11.0 |
| 6. Ferric Oxide Pigment | 3.0 | 3.0 |
| 7. Cetiol-A | 0.2 | 0.2 |
| 8. Phenyl Dimethicone | 0.3 | 0.3 |
| 9. Preservative | 0.1 | 0.1 |
| 10. Aromatics | Microdose | Microdose |

(1) Components 1 to 6 were powdered once with a hammer-type powdering machine.

(2) The resulting material of the above step (1) was vigorously mixed for 5 minutes in a high-speed mixer.

(3) Components 7 to 10 were mixed with the resulting material of the step (2) and heated.

(4) The resulting material of the step (3) was vigorously mixed for 5 minutes in the high-speed mixer.

(5) The resulting material of the step (4) was powdered twice with the hammer-type powdering machine.

As described above, the particles surface-treated up to 3% to the maximum with the amino acid silicon polymer prepared by reacting an amino acid and a functional silicon polymer in the manner of organic synthesis have water resistance and usability peculiar to silicon-treated pigments and take positive surface charges, thereby offering good adhesion to the skin and durability. Due to these characteristics, the cosmetic containing the surface-treated particles of the present invention is superior in the cosmetic effect to that containing the conventional surface-treated particles.

What is claimed is:

1. An amino acid silicon polymer having a formula:

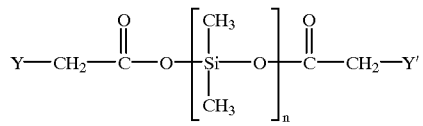

wherein "n" is an integer from 1 to 1000, and Y and Y' have an amino acid group at their terminals.

2. The amino acid silicon polymer as defined in claim 1, wherein Y and Y' are either

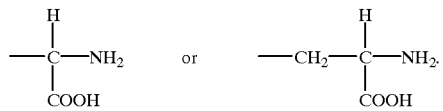

3. A method of preparing an amino acid silicon polymer of claim 2, comprising:

esterifying dimethyl polysiloxanol having Formula 1 with at least one of amino acids having Formula 2 in an organic solvent in the presence of a catalyst:

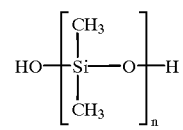

[Formula 1]

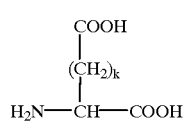

[Formula 2]

wherein "n" is an integer from 1 to 1000, and wherein k is 1 or 2.

4. The method as defined in claim 3, wherein the catalyst is selected from the group consisting of sulfuric acid, paratoluene sulfonic acid, methane sulfonic acid, tin, zinc, titanium, organic titanium, organic tin, zinc oxide, magnesium oxide and calcium oxide.

5. The method as defined in claim 3, wherein the organic solvent is selected from the group consisting of benzene, toluene, xylene, 1,4-dioxane, chloroform and 1,2-dichloroethane.

6. The amino acid silicon polymer as defined in claim 1, wherein Y and Y' are ones selected from the group consisting of:

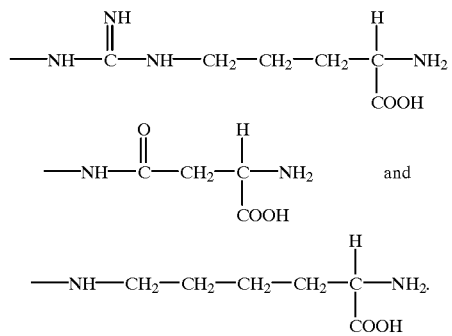

7. A method for preparing an amino acid silicon polymer of claim 6, comprising:

reacting dimethyl polysiloxanol dichloroacetate of Formula 6 with at least one amino acids of Formula 7 in the presence of a weak basic catalyst:

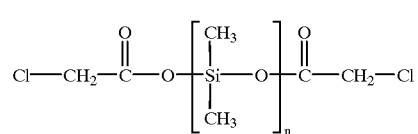

[Formula 6]

wherein "n" is an integer from 1 to 1000;

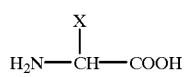

[Formula 7]

wherein X is one selected from the group consisting of:
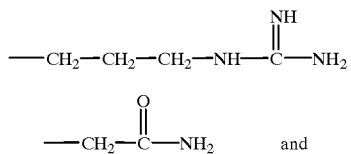
and
—CH₂—CH₂—CH₂—CH₂—NH₂.
8. The method as defined in claim 7, wherein the weak basic catalyst is selected from the group consisting of sodium carbonate, sodium bicarbonate and potassium carbonate.
* * * * *

UNITED STATES PATENT AND TRADEMARK OFFICE
CERTIFICATE OF CORRECTION

PATENT NO. : 6,268,454 B1
DATED : July 31, 2001
INVENTOR(S) : Song et al.

It is certified that error appears in the above-identified patent and that said Letters Patent is hereby corrected as shown below:

Title page,
Item [57], ABSTRACT,
Line 11, please replace "silicon" with -- silicone --.

Column 1,
Line 59, after "silicon" please insert -- polymer or silicone --.

Column 2,
Line 20, please replace "silicon" with -- silicone --.

Column 3,
Lines 11 and 19, please replace "silicon" with -- silicone --.

Column 8,
Lines 33, 37 and 39, please replace "silicon" with -- silicone --.

Column 11,
Lines 38 and 45, please replace "silicon" with -- silicone --.

Column 13,
Line 5, please replace "silicon" with -- silicone --.

Signed and Sealed this

Twenty-third Day of September, 2003

JAMES E. ROGAN
*Director of the United States Patent and Trademark Office*